United States Patent [19]

Heeres et al.

[11] Patent Number: 4,503,055

[45] Date of Patent: Mar. 5, 1985

[54] DERIVATIVES OF [4-(PIPERAZIN-1-YL-PHENYLOXYME-THYL)-1,3-DIOXOLAN-2-YLMETHYL]-1H-IMIDAZOLES AND 1H-1,2,4-TRIAZOLES

[75] Inventors: Jan Heeres, Vosselaar; Joseph Mostmans, Antwerp, both of Belgium

[73] Assignee: Janssen Pharmaceutica, N.V., Beerse, Belgium

[21] Appl. No.: 306,267

[22] Filed: Sep. 28, 1981

Related U.S. Application Data

[63] Continuation of Ser. No. 23,807, Mar. 26, 1979, abandoned, which is a continuation-in-part of Ser. No. 921,380, Jul. 3, 1978, abandoned.

[51] Int. Cl.$^3$ .................. A61K 31/415; C07D 405/14
[52] U.S. Cl. ..................................... 514/285; 544/121; 544/364; 544/366; 544/370; 514/240
[58] Field of Search ............... 544/364, 366, 370, 121; 424/250, 248.5, 248.51, 248.54, 248.55, 248.58

[56] References Cited

U.S. PATENT DOCUMENTS

| | | | |
|---|---|---|---|
| 2,603,652 | 7/1952 | Schechter et al. | 424/311 |
| 3,936,470 | 2/1976 | Heeres et al. | 424/273 |
| 4,144,346 | 3/1979 | Heeres et al. | 424/273 |
| 4,243,806 | 1/1981 | Raeymaekers et al. | 544/364 |

Primary Examiner—Glennon H. Hollrah
Assistant Examiner—James H. Turnipseed
Attorney, Agent, or Firm—Geoffrey G. Dellenbaugh

[57] ABSTRACT

Novel derivatives of 4-(piperazin-1-yl-phenyloxymethyl)-1,3-dioxolan-2-ylmethyl-1H-imidazoles and 1H-1,2,4-triazoles, useful as antifungal and antibacterial agents.

6 Claims, No Drawings

DERIVATIVES OF [4-(PIPERAZIN-1-YL-PHENYLOXYMETHYL)-1,3-DIOXOLAN-2-YLMETHYL]-1H-IMIDAZOLES AND 1H-1,2,4-TRIAZOLES

CROSS-REFERENCE TO RELATED APPLICATIONS

This is a continuation of application Ser. No. 23,807, filed Mar. 26, 1979, now abandoned, which in turn is a continuation-in-part of Ser. No. 921,380, filed July 3, 1978, now abandoned.

BACKGROUND OF THE INVENTION

In U.S. Pat. No. 3,936,470 and Belg. Pat. No. 837,831 there are described a number of 1-(1,3-dioxolan-2-ylmethyl)-1H-imidazoles and 1H-1,2,4-triazoles having antifungal and antibacterial properties. The compounds of this invention differ from the foregoing essentially by the substitution of the aryloxy-moiety with a piperazinyl group, substituted in the 4-position with an aliphatic group or a sulfonyl group. Other similar compounds are described in U.S. Pat. No. 4,144,346. The compounds of this invention differ from the latter essentially by the nature of the Y-substituent on the piperazine nitrogen atom.

DESCRIPTION OF THE PREFERRED EMBODIMENTS

This invention is concerned with novel 1H-imidazole and 1H-1,2,4-triazole derivatives which may structurally be represented by the formula:

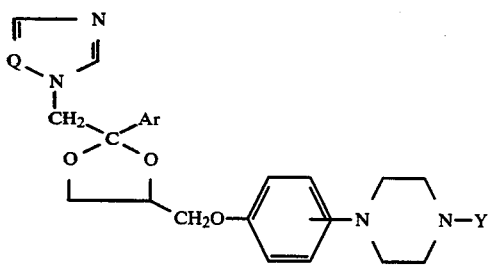
(I)

and the pharmaceutically acceptable acid addition salts and stereochemically isomeric forms thereof,
wherein:
Q is a member selected from the group consisting of N and CH;
Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and
the radical Y is a member selected from the group consisting of:
a radical of the formula $$-SO_2-R^1 \quad (a)$$

wherein $R^1$ is selected from the group consisting of trifluoromethyl and aryl;
a radical of formula $$-alk-R^2 \quad (b)$$

wherein alk is a member selected from the group consisting of lower alkylene and lower alkenylene and $R^2$ is a member selected from the group consisting of cyano, amino, mono- and di(lower alkyl)amino, arylamino, mono- and di(aryllower alkyl)amino, 1-pyrrolidinyl, 1-morpholinyl, 1-piperidinyl, aryloxy and aryl, provided that alk is other than methylene when $R^2$ is phenyl;
a radical of formula $$-C_nH_{2n}-\overset{\overset{\displaystyle X}{\|}}{C}-R^3 \quad (c)$$

wherein n is an integer of from 0 to 6 inclusive, X is O or S and $R^3$ is selected from the group consisting of hydrogen, mono-, di- and trihalolower alkyl, amino, mono- and di(lower alkyl)amino, arylamino, mono- and di(aryllower alkyl)amino, aminolower alkyl, mono- and di(lower alkyl)aminolower alkyl, (1-pyrrolidinyl)lower alkyl, (1-morpholinyl)lower alkyl, (1-piperidinyl)lower alkyl, aryl, aryllower alkyl, aryllower alkenyl and lower alkyloxycarbonyllower alkyloxy, provided that:
(i) said n is other than 0 or 1 when said $R^3$ is amino or lower alkylamino; and
(ii) said n is other than 0 when said $R^3$ is di(lower alkyl)amino or aryl; and
a radical of formula $$-C_mH_{2m}-A-\overset{\overset{\displaystyle X}{\|}}{C}-R^4 \quad (d)$$

wherein m is an integer of from 1 to 6 inclusive, A is O or NH, X is O or S and $R^4$ is a member selected from the group consisting of hydrogen, lower alkyl, lower alkyloxy, aryl, aryloxy, aryllower alkyl, amino, mono- and di(lower alkyl)amino, arylamino, mono- and di(aryllower alkyl)amino, 1-pyrrolidinyl, 1-morpholinyl and 1-piperidinyl;
wherein said aryl, as used in the foregoing definitions, is selected from the group consisting of phenyl, substituted phenyl, thienyl, halothienyl, lower alkylthienyl and pyridinyl, said substituted phenyl having from 1 to 3 substituents each independently selected from the group consisting of lower alkyl, lower alkyloxy, halo, amino, mono- and di(lower alkyl)amino, lower alkylcarbonylamino, nitro and trifluoromethyl.

The preferred compounds of this invention are those wherein the 1-piperazinyl group is attached to the 4-position of the phenoxymethyl moiety.

As used herein the term "halo" is generic to halogens of atomic weight less than 127, i.e., fluoro, chloro, bromo and iodo; the term "lower alkyl" denotes straight and branch chained hydrocarbon radicals having from 1 to 6 carbon atoms such as, for example, methyl, ethyl, 1-methylethyl, 1,1-dimethylethyl, propyl, butyl, pentyl, hexyl and the like; and the term "lower alkenyl" denotes straight and branched alkenyl radicals having from 2 to 6 carbon atoms such as, for example, ethenyl, 2-propenyl, 3-butenyl, 3-methyl-2-pentenyl and the like.

In order to simplify the structural representation of compounds (I) and of certain starting materials and intermediates used in the preparation thereof, the 2-Ar-2-(1H-imidazol-1-yl-methyl or 1H-1,2,4-triazol-1-ylmethyl)-1,3-dioxolan-4-yl group, wherein Ar is as previously defined, will hereafter be represented by the symbol D:

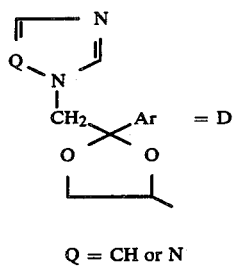

Q = CH or N

The compounds of formula (I) wherein Y has the previously defined meaning, can generally be prepared by O-alkylating an appropriately substituted phenol of formula (III) with an appropriate reactive ester of formula (II), following standard O-alkylation procedures.

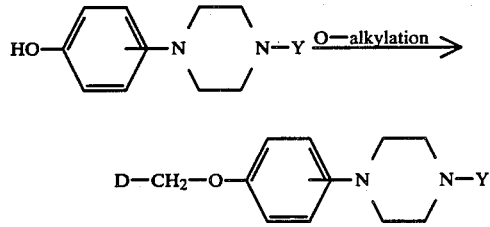

In formula (II), W has the meaning of a reactive ester residue such as, for example, halo, methylsulfonyloxy, 4-methylphenylsulfonyloxy and the like. The reaction of (II) with (III) is carried out under art-known conditions of performing O-alkylations with reactive esters. The reaction is generally carried out in an appropriate reaction-inert organic solvent, such as, for example, N,N-dimethylformamide, N,N-dimethylacetamide, hexamethylphosphoric triamide, dimethylsulfoxide, 4-methyl-2-pentanone and the like, optionally in admixture with other reaction inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

The compounds of formula (I) may also be prepared by the reaction of an appropriate piperazine (IV) with an appropriate reactant of formula (V), wherein W has the meaning of a reactive ester, as previously described.

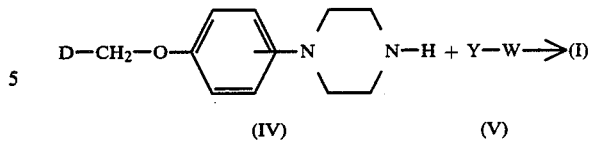

In said reaction the meaning of W as well as the reaction-conditions depend upon the nature of Y as will be explained hereafter.

In case Y is other than a radical of formula (a), other than a radical of formula (c) wherein n is 0 and other than a radical of formula (c) wherein n is 1 and $R^3$ is lower alkyloxycarbonyllower alkyloxy, W may be halo, or a sulfonyloxy group and the reaction is then preferably conducted in a suitable reaction-inert solvent such as, for example, a lower alkanol, e.g., ethanol, butanol and the like; an amide, e.g., N,N-dimethylformamide and the like; a ketone, e.g., 4-methyl-2-pentanone and the like; dimethylsulfoxide; a halogenated hydrocarbon, e.g., dichloromethane and the like. Said solvents may be used as such or in admixture with other reaction-inert solvents such as, for example, aromatic and aliphatic hydrocarbons, e.g., hexane, benzene and the like. Somewhat elevated temperatures may be advantageous to enhance the rate of the reaction and, most preferably, the reaction is carried out at from about 80° C. to about 130° C. Further it may be advantageous to add an appropriate base such as, for example, an amine, e.g., N,N-diethylethanamine and the like, pyridine and the like; an alkali metal- or an earth alkaline metal carbonate or hydrogen carbonate, e.g., sodium carbonate, potassium hydrogen carbonate and the like.

In a particular case, when W represents a very reactive leaving group such as halo in α-position of a carbonyl function, and when carbon dioxide or a carbonate or a hydrogen carbonate is present in the reaction medium, there may occur an insertion-reaction of said carbon dioxide. In such manner the compounds of formula (I) wherein Y represents a radical of formula (c) wherein n is 1 and $R^3$ is a lower alkyloxycarbonyllower alkyloxy radical may be prepared by the reaction of an appropriate piperazine of formula (IV) with a reagent of formula (V) wherein Y is lower alkyloxycarbonyllower alkyl in the presence of carbon dioxide or a suitable carbonate or hydrogen carbonate.

In case Y represents a radical of formula (a) or a radical of formula (c) wherein n is 0, then W is selected from the group consisting of halo, most preferably chloro, and the reaction is preferably conducted in a suitable reaction-inert solvent such as, for example, an aliphatic-, an alicyclic- or an aromatic hydrocarbon, e.g., hexane, cyclohexane, benzene and the like; a halogenated hydrocarbon, e.g., trichloromethane and the like. More particularly, when Y is a radical of formula (a), the solvent may even so be selected from the group consisting of water; a lower alkanol, e.g., ethanol and the like, and an amide, e.g., dimethylacetamide and the like.

The compounds of formula (I) wherein Y represents a radical (b) wherein alk is as previously defined and wherein $R^2$ is a previously defined, but other than cyano and other than aryl, said $R^2$ being represented by $R_a^2$ and said compounds by the formula (I-a), may be prepared by substituting the reactive leaving group W in an intermediate of formula (VI) by an appropriately substituted amine or alcohol of formula (VII), following art-known O-, respectively N-alkylation procedures as previously described herein.

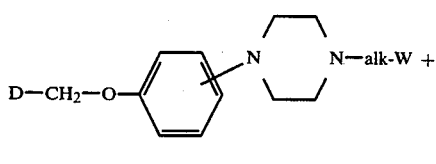

(VI)

H—$R_a^2$ $\xrightarrow{\text{O— or N—alkylation}}$ (VII)

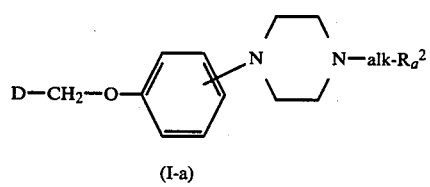

(I-a)

The compounds of formula (I-a) wherein $R_a^2$ is amino can, more preferably, be prepared by reacting (VI) with ammonia wherein 2 protons have been replaced by protective groups, such as, for example, di(phenylmethyl)amine, 1H-isoindole-1,3(2H)-dione and the like, and subsequently eliminating the protective groups following art-known procedures, depending upon the nature of said protecting groups, e.g., by catalytic hydrogenation or by alkaline hydrolysis.

Said primary amine derivatives of formula (I-a) may also be derived from the corresponding cyanides by reducing the latters following art-known cyano-to-amine reduction procedures such as, catalytic hydrogenation and the like.

The compounds of formula (I-a) wherein $R_a^2$ is amino, mono- and di(lower alkyl)amino, arylamino, mono- and di(aryllower alkyl)amino, 1-pyrrolidinyl, 1-morpholinyl or 1-piperidinyl may also be prepared starting from an appropriate carbonyl compound and ammonia or an appropriately substituted primary or secondary amine following art-known reductive amination procedures, i.e., by catalytically hydrogenating the starting materials in the presence of an appropriate catalyst, e.g., platina-on-charcoal and the like.

The compounds of formula (I) wherein Y represents a radical (d) wherein A and $R^4$ are as previously defined and wherein X is O, said compounds being represented by the formula (I-b), may easily be prepared by the reaction of an amine or an alcohol of formula (VIII) with an appropriately substituted carboxylic acid of formula $R^4$—COOH  (IX)

or a functional derivative thereof, most desirable, its acyl halide

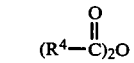

or its anhydride

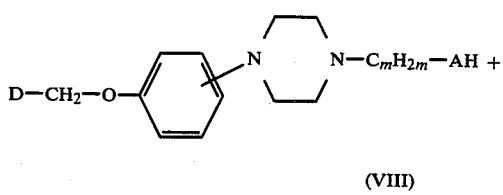

The reaction may be carried out by stirring and heating the reactants together in the presence of a suitable reaction-inert solvent such as, for example, a halogenated hydrocarbon, e.g., dichloromethane and the like.

When an acyl halide of formula (IX-a) is used, it may be advantageous to add a base, such as, for example, an amine, e.g., N,N-diethylethanamine and the like, in order to neutralize the liberated hydrohalic acid.

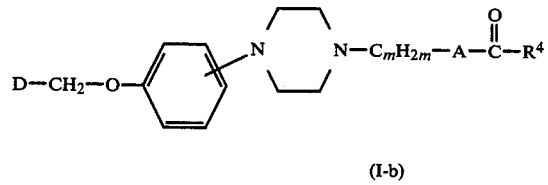

(VIII)

(IX) or
(IX-a) or $\longrightarrow$
(IX-b)

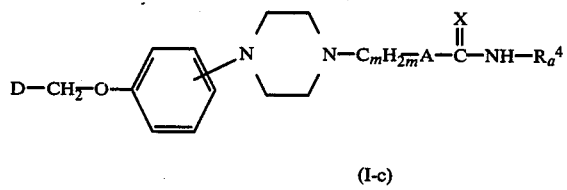

(I-b)

The compounds of formula (I) wherein Y represents a radical (d) wherein A and X are as previously defined and $R^4$ is amino, lower alkylamino, arylamino or aryllower alkylamino, said $R^4$ being represented by —NH-$R_a^4$ and said compounds by the formula (I-c), may conveniently be prepared by the addition-reaction of an appropriate amine or alcohol of formula (VIII) with an appropriately substituted isocyanate or isothiocyanate of formula (X).

(VIII) + $R_a^4$—N=C=X $\xrightarrow{\text{addition}}$ (X)

(I-c)

The addition-reaction is preferably carried out by stirring and heating the reactants together in the presence of a suitable reaction-inert solvent such as, for example, an aromatic hydrocarbon, e.g., methylbenzene and the like; an halogenated hydrocarbon, e.g., dichloromethane and the like; acetonitrile and the like. In order to enhance the rate of the reaction it may be advantageous to add an amine, e.g. diethyl ethanamine, to the reaction mixture.

Furthermore certain compounds of formula (I) may be derived from other compounds of formula (I) by art-known functional group transformations, e.g., the compounds of formula (I) wherein Y represents a radical (a) wherein $R^1$ is aminophenyl may be derived from the corresponding lower alkylcarbonylamino derivatives by alkaline hydrolysis.

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparation will be described hereafter.

The intermediates of formula (III) can generally be derived from the corresponding methoxy derivative (XI) by converting the latter into the corresponding phenols (III) using, e.g., a strong non-oxidizing acid such as, for example, hydrobromic acid in glacial acetic acid.

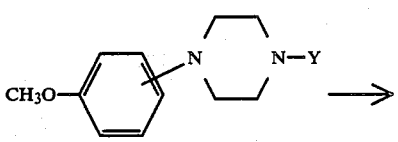

(XI)

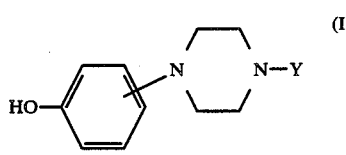

(III)

The intermediates of formula (XI) used as starting materials herein, can be obtained by N-substituting an appropriate piperazine (XII) with a reactant of the formula (V) wherein W is a reactive leaving group, as previously defined.

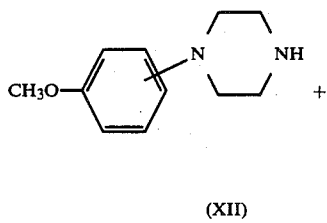

(XII)

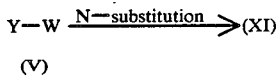

The intermediates of formula (III) can alternatively be prepared by the reaction of an appropriate piperazine (XII-a) with a reactant of the formula (V), following the previously described procedure herein for the synthesis of (I) starting from (IV) and (V).

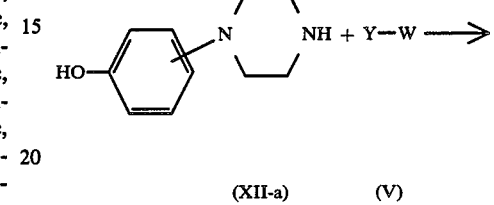

(XII-a)  (V)

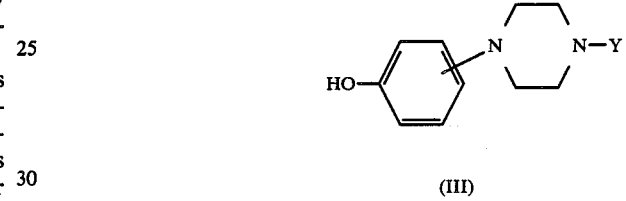

(III)

The intermediates of formula (IV) can generally be prepared by O-alkylating an appropriately substituted phenol (XII-b), wherein P represents a protective group, with an appropriate reactive ester (II), following standard O-alkylation procedures, as previously described herein for the synthesis of (I) starting from (II) and (III), and subsequently eliminating the protective group of the thus obtained (XIII), following art-known procedures.

(II)

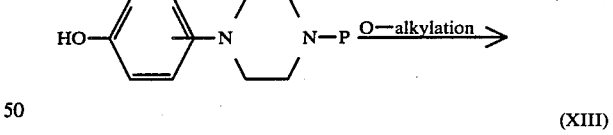

(XII-b)

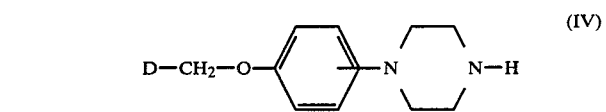

(XIII)

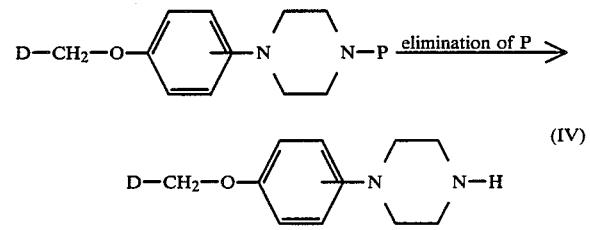

(IV)

The intermediates of formula (VIII) can generally be derived from an intermediate (IV) by alkylating the latter with an appropriate reactive ester of formula (XIV), wherein m and W are as previously defined, following standard N-alkylating procedures as previously described herein for the synthesis of (I) starting from (IV) and (V).

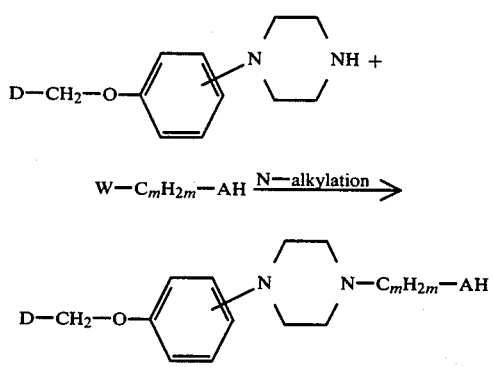

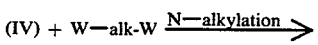

When m in formula (VIII) is 2, the same intermediates (VIII) may also be prepared by the reaction of (IV) with oxirane, respectively aziridine, e.g., by bubbling them through a heated solution of (IV) in a suitable organic solvent such as a lower alkanol, e.g., methanol, ethanol, 2-propanol and the like.

Following the same procedure the intermediates of formula (VI) may be derived from an intermediate (IV) by N-alkylating the latter with an appropriate reactive ester of formula (XV) wherein W, and alk are as previously defined.

(IV) + W—alk-W $\xrightarrow{\text{N—alkylation}}$ (XV)

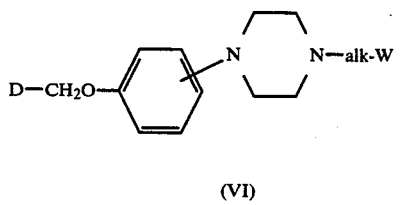

(VI)

Starting materials of formula (II) wherein Q stands for CH and methods of preparing the same are described in U.S. Pat. No. 4,144,346. In general the reactive ester of formula (II) can be prepared along the following sequence of reactions.

An appropriate 1-Ar-2-bromoethanone of formula (XVI) is subjected to a ketalization reaction with 1,2,3-propanetriol following methodologies analogous to those described in Synthesis, 1974, (I) 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as hexane.

The thus obtained dioxolane (XVII) is then reacted with benzoyl chloride to obtain a benzoate of the formula (XVIII) and the latter is subsequently reacted with 1H-imidazole or 1H-1,2,4-triazole.

Said reaction is preferably carried out by stirring and heating the reactants together in a suitable organic solvent, e.g., N,N-dimethylformamide, in the presence of an appropriate strong metal base, e.g., sodium methanolate, to obtain an intermediate of the formula (XIX).

The desired reactive esters of formula (II) are then conveniently prepared by first hydrolyzing (XIX) in alkaline medium and thereafter converting the hydroxy group of the thus obtained (XX) into a reactive ester thereof according to methodologies generally known in the art.

For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, thionyl chloride, sulfuryl chloride, phosphor pentachloride, phosphor pentabromide, phosphoryl chloride and the like.

When the reactive ester is an iodide, it is preferably derived from the corresponding chloride or bromide by the replacement of that halogen with iodine.

The foregoing reactions may be illustrated as follows:

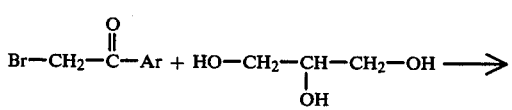

-continued

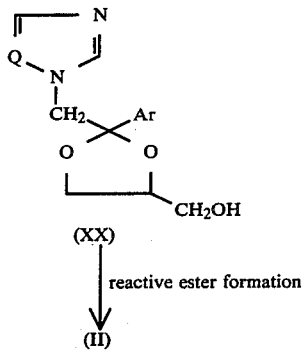

From formula (I) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g., column-chromatography.

Since the stereochemical configuration is already fixed in the intermediates (II) and (IV) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diasteromeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans, Mucor* species, *Aspergillus fumigatus, Sporotricum schenckii* and Saprolegnia species, and against bacteria such as, for example, *Erysipelotrix insidiosa*, Staphylococci such as *Staphylococcus hemolyticus* and Streptococci such as *Streptococcus pyogenes. In view of their potent, local as well as systemic, antimicrobial activity the compounds of this invention constitute useful tools for the destruction or prevention of the growth of fungi and bacteria and more particularly they can effectively be used in the treatment of subjects suffering from such microorganisms.*

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

EXPERIMENT A

Activity of compounds (I) against vaginal candidosis in rats

Female Wistar rats of ±100 g body weight are used. They are ovariectomized and hysterectomized and after three weeks of recovery, 100 μg of oestradiol undecylate in sesame oil is given subcutaneously once a week for 3 consecutive weeks. The thus induced pseudooestrus is controlled by microscopic examination of vaginal smears. Food and water are left available ad libitum. The rats are infected intravaginally with $8.10^5$ cells of Candida albicans, grown on Sabouraud broth for 48 hours at 37° C. and diluted with saline. The date of infection varies from day +25 to day +32 after surgical intervention, depending on the appearance of signs of induced pseudooestrus.

The drugs under investigation are administered orally once a day for two days starting from the day of infection. For each experiment there are placebo treated controls. The results are assessed by taking vaginal smears with sterile swabs on several days after the infection. The swabs are put into Sabouraud broth in petri-dishes and incubated for 48 hours at 37° C. If no growth of Candida albicans occurs, i.e., when the animals are negative at the end of the experiment, this is due to drug administration because it never happens in placebo treated controls.

The table below gives the lowest oral dose of the drug under investigation which is found active at the 14th day after infection.

EXPERIMENT B

Activity of compounds (I) against crop candidosis in turkeys

Turkeys of 14 days old are infected in the crop with $4.10^6$ Candida albicans cells, grown on Sabouraud broth for 48 hours at 37° C. and diluted with saline. The volume of the inoculum is 1 ml. The drugs under investigation are premixed in 500 mg of lacton and thereafter admixed in 1000 g of meal without any additives. The concentration of the drug under investigation in the meal is expressed in mg/kg.

The animals are given the medicated feed for 13 consecutive days starting on the day of infection. At the end of the experiment all animals are sacrificed. At autopsy the crops are removed, emptied and grinded in an ultra-turrax mixer in 15 ml of sterile saline. Colony counting is done on Sabouraud agar and the results given in the table represents the $ED_{50}$, i.e., the dose of the drug whereby the crops of 50% of the animals are completely negative for Candida albicans.

The compounds listed in the table are intended to illustrate and not to limit the scope of the present invention.

[Structure: Q-N(imidazole-CH2)-C(2,4-dichlorophenyl)(CH2-O-C6H4-N(piperazine)N-Y), cis-1,3-dioxolane]

| Y | Q | Vaginal candidosis in rats: lowest effective dose in mg/kg orally | Crop candidosis in turkeys: ED$_{50}$ in mg/kg feed |
|---|---|---|---|
| $\overset{O}{\underset{\|}{C}}$—O—CH$_2$—$\overset{O}{\underset{\|}{C}}$—OC$_2$H$_5$ | CH | 2.5 | 31 |
| CH$_2$—CO—NH—(C$_6$H$_4$)—CH$_3$ (ortho CH$_3$) | CH | 2.5 | 16 |
| CH$_2$—CO—NH—(C$_6$H$_4$)—CH$_3$ (para) | CH | — | 16 |
| CH$_2$—CO—NH—(2,6-dichlorophenyl) | CH | 2.5 | 31 |
| $\overset{O}{\underset{\|}{C}}$—CH=CH—(C$_6$H$_4$)—Cl | N | — | 16 |
| CH$_2$—(C$_6$H$_4$)—Cl | CH | — | <31 |
| $\overset{O}{\underset{\|}{\underset{O}{S}}}$—(C$_6$H$_4$)—CH$_3$ | N | — | <31 |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention. Unless otherwise stated all parts therein are by weight.

A. PREPARATION OF INTERMEDIATES

EXAMPLE I

To a stirred mixture of 15.5 parts of 4-(1-piperazinyl)-phenol dihydrobromide, 40 parts of ethanol and 75 parts of water are added 15.2 parts of 4-methylbenzenesulfonyl chloride and stirring is continued for 30 minutes at room temperature. Then there are added portionwise 12.6 parts of sodium hydrogen carbonate at 0° C. Upon completion, stirring is continued overnight at room temperature. The precipitated product is filtered off and taken up in alkaline water. The mixture is filtered over hyflo and the filtrate is acidified with acetic acid. The precipitated product is filtered off and taken up in water. The free base is liberated in the conventional manner with a sodium hydroxide solution. The whole is filtered over hyflo and the filtrate is acidified with acetic acid. The precipitated product is filtered off and dried, yielding 4.8 parts of 1-(4-hydroxyphenyl)-4-(4-methylphenylsulfonyl)piperazine; mp. 193.1° C.

EXAMPLE II

To a stirred mixture of 34 parts of 4-(1-piperazinyl)-phenol dihydrobromide, 100 parts of water and 130 parts of dichloromethane are added portionwise 42 parts of sodium hydrogen carbonate. Then there is added dropwise (slowly) a solution of 19 parts of chloroacetic acid anhydride in dichloromethane. Upon completion, stirring is continued for 1 hour at room temperature. The precipitated product is filtered off and crystallized from 4-methyl-2-pentanone, yielding 11 parts of 1-(2-chloroacetyl)-4-(4-hydroxyphenyl)piperazine.

A mixture of 10 parts of 1-(2-chloroacetyl)-4-(4-hydroxyphenyl)piperazine, 6.9 parts of morpholine and 40 parts of methanol is stirred and heated for 2 hours at 50° C. The reaction mixture is evaporated and the residue is stirred with water. The precipitated product is filtered off, dried on the filter and crystallized from 2-propanol, yielding 5.5 parts of 1-(4-hydroxyphenyl)-4-[(4-morpholinyl)acetyl]piperazine; mp. 197.3° C.

EXAMPLE III

A mixture of 3.4 parts of methanesulfonyl chloride and 100 parts of pyridine is stirred till all solid enters solution. Then there are added slowly 13 parts of cis-4-{4-[2-(2,4-dichlorophenyl)-2-(1H-imidazol-1-ylmethyl)-1,3-dioxolan-4-ylmethoxy]phenyl}-1-piperazineethanol while cooling. The whole is stirred overnight at room temperature. The reaction mixture is evaporated and the residue is stirred with water. The oily product solidifies upon scratching. It is filtered off and crystallized from 4-methyl-2-pentanone, yielding 4 parts of cis-1-(2-chloroethyl)-4-{4-[2-(2,4-dichlorophenyl)-2-(1H-imidazol-1-ylmethyl)-1,3-dioxolan-4-ylmethoxy]phenyl}piperazine; mp. 130.6° C.

A mixture of 2 parts of 1H-isoindole-1,3(2H)-dione, potassium salt, 6 parts of cis-1-(2-chloroethyl)-4-{4-[2-(2,4-dichlorophenyl)-2-(1H-imidazol-1-ylmethyl)-1,3-dioxolan-4-ylmethoxy]phenyl}piperazine and 100 parts of dimethyl sulfoxide is stirred and heated overnight at 60° C. The reaction mixture is poured onto water and the whole is stirred for 10 minutes. The precipitated product is filtered off and dissolved in dichloromethane. The latter is dried, filtered and evaporated. The oily residue is purified by column-chromatography over silica gel using a mixture of trichloromethane and methanol (95:5 by volume) as eluent. The pure fractions are collected and the eluent is evaporated. The oily residue is crystallized from 2-propanol, yielding 4 parts of cis-2-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-1H-isoindole-1,3(2H)-dione; mp. 169.1° C.

B. PREPARATION OF FINAL COMPOUNDS

EXAMPLE IV

To a stirred mixture of 4.1 parts of cis-[2-(2,4-dichlorophenyl)-2-(1H-1,2,4-triazol-1-ylmethyl)-1,3-dioxolan-4-ylmethyl]methanesulfonate and 100 parts of dimethyl sulfoxide are added 0.25 parts of sodium hydride dispersion 76% and the whole is stirred and heated for 30 minutes at 50° C. After cooling, 4 parts of 1-(4-hydroxyphenyl)-4-(4-methylphenylsulfonyl)piperazine are added and the whole is stirred and heated overnight at 100° C. The reaction mixture is cooled and poured onto water. The product is extracted twice with benzene. The combined extracts are washed twice with a diluted sodium hydroxide solution and twice with water, dried, filtered and evaporated. The residue is converted into the hydrochloride salt in 2-propanol and 2,2'-oxybispropane. The salt is filtered off and crystallized from acetonitrile, yielding 2 parts of cis-1-{4-[2-(2,4-dichlorophenyl)-2-(1H-1,2,4-triazol-1-ylmethyl)-1,3-dioxolan-4-ylmethoxy]phenyl}-4-(4-methylphenylsulfonyl)piperazine dihydrochloride hemihydrate; mp. 187.5° C.

Following the same procedure and using equivalent amounts of 1-(4-hydroxyphenyl)-4-[(4-morpholinyl)acetyl]piperazine and cis-[2-(2,4-dichlorophenyl)-2-(1H-imidazol-1-ylmethyl)-1,3-dioxolan-4-ylmethyl]methanesulfonate there is also prepared:

cis-1-{4-[2-(2,4-dichlorophenyl)-2-(1H-imidazol-1-ylmethyl)-1,3-dioxolan-4-ylmethoxy]phenyl}-4-[2-(4-morpholinyl)acetyl]piperazine trinitrate; mp. 200° C.

EXAMPLE V

A mixture of 2.6 parts of 4-(acetylamino)benzenesulfonyl chloride, 4.9 parts of cis-1-{4-[2-(2,4-dichlorophenyl)-2-(1H-imidazol-1-ylmethyl)-1,3-dioxolan-4-ylmethoxy]phenyl}-piperazine, 4 parts of potassium carbonate, 150 parts of trichloromethane and 100 parts of water is stirred for 2 hours at room temperature. The reaction mixture is diluted with water and the whole is stirred for another 2 hours at room temperature. The layers are separated and the organic phase is dried, filtered and evaporated. The residue is triturated in 4-methyl-2-pentanone. The product is filtered off and crystallized from 4-methyl-2-pentanone, yielding 6 parts (87%) of cis-N-{4-[4-{4-[2-(2,4-dichlorophenyl)-2-(1H-imidazol-1-ylmethyl)-1,3-dioxolan-4-ylmethoxy]phenyl}-1-piperazinylsulfonyl]phenyl}acetamide; mp. 205.8° C.

Following the same N-alkylation-procedure and using equivalent amounts of the appropriate starting materials there are also prepared:

cis-1-{4-[2-(2,4-dichlorophenyl)-2-(1H-imidazol-1-ylmethyl)-1,3-dioxolan-4-ylmethoxy]phenyl}-4-(phenylsulfonyl)piperazine ethanedioate (1:2); mp. 182.5° C.;

cis-1-{4-[2-(2,4-dichlorophenyl)-2-(1H-imidazol-1-ylmethyl)-1,3-dioxolan-4-ylmethoxy]phenyl}-4-(4-methylphenylsulfonyl)piperazine; mp. 123.9° C.;

cis-1-{4-[2-(2,4-dichlorophenyl)-2-(1H-1,2,4-triazol-1-ylmethyl)-1,3-dioxolan-4-ylmethoxy]phenyl}-4-(phenylsulfonyl)piperazine; mp. 140.6° C.; and cis-N-{4-[4-{4-[2-(2,4-dichlorophenyl)-2-(1H-1,2,4-triazol-1-ylmethyl)-1,3-dioxolan-4-ylmethoxy]phenyl}-1-piperazinylsulfonyl]phenyl}acetamide; mp. 183.5° C.

EXAMPLE VI

A mixture of 1.8 parts of 2,2-dichloroacetyl chloride, 4.9 parts of cis-1-{4-[2-(2,4-dichlorophenyl)-2-(1H-imidazol-1-ylmethyl)-1,3-dioxolan-4-ylmethoxy]phenyl}piperazine, 2 parts of potassium carbonate and 150 parts of trichloromethane is stirred overnight at room temperature. Then there are added 50 parts of water and the layers are separated. The organic phase is dried, filtered and evaporated. The residue is purified by column-chromatography over silica gel using a mixture of trichloromethane and methanol (97:3 by volume) as eluent. The pure fractions are collected and the eluent is evaporated. The residue is converted into the ethanedioate salt in 2-propanone and 2,2'-oxybispropane. The salt is filtered off and crystallized from acetonitrile, yielding 3.6 parts (45%) of cis-1-(dichloroacetyl)-4-{4-[2-(2,4-dichlorophenyl)-2-(1H-imidazol-1-ylmethyl)-1,3-dioxolan-4-ylmethoxy]phenyl}piperazine ethanedioate (1:2) monohydrate; mp. 98.9° C.

In a similar manner there are also prepared:

cis+trans-1-[3-(4-chlorophenyl)-1-oxo-2-propenyl]-4-{4-[2-(2,4-dichlorophenyl)-2-(1H-1,2,4-triazol-1-ylmethyl)-1,3-dioxolan-4-ylmethoxy]phenyl}piperazine; mp. 180.1° C.; and cis-1-(dichloroacetyl)-4-{4-[2-(2,4-dichlorophenyl)-2-(1H-1,2,4-triazol-1-ylmethyl)-1,3-dioxolan-4-ylmethoxy]phenyl}piperazine; mp. 142.4° C.

EXAMPLE VII

A mixture of 4.9 parts of trifluoromethanesulfonyl chloride, 2.1 parts of cis-1-{4-[2-(2,4-dichlorophenyl)-2-(1H-1,2,4-triazol-1-ylmethyl)-1,3-dioxolan-4-ylmethoxy]phenyl}piperazine and 100 parts of pyridine is stirred overnight at room temperature. The reaction mixture is poured onto water and the product is extracted with benzene. The extract is washed with water, dried, filtered and evaporated. The residue is purified by column-chromatography over silica gel using a mixture of methylbenzene and ethanol (95:5 by volume) as eluent. The pure fractions are collected and the eluent is evaporated. The residue is stirred in 2,2'-oxybispropane. The product is filtered off and dried, yielding 1.2 parts of cis-1-{4-[2-(2,4-dichlorophenyl)-2-(1H-1,2,4-triazol-1-ylmethyl)-1,3-dioxolan-4-ylmethoxy]phenyl}-4-(trifluoromethylsulfonyl)piperazine; mp. 166.9° C.

EXAMPLE VIII

A mixture of 1.34 parts of ethyl 2-chloroacetate, 5 parts of cis-1-{4-[2-(2,4-dichlorophenyl)-2-(1H-imidazol-1-ylmethyl)-1,3-dioxolan-4-ylmethoxy]phenyl}piperazine, 2.75 parts of potassium carbonate and 50 parts of dimethyl sulfoxide is stirred and heated for 1 hour at 60° C. The reaction mixture is poured onto ice-water and the product is extracted with dichloromethane. The extract is washed with water, dried, filtered and evaporated. The oily residue is purified by column-chromatography over silica gel using a mixture of methylbenzene and ethanol (90:10 by volume) as eluent. The pure fractions are collected and the eluent is evaporated. The oily residue is crystallized from 4-methyl-2-pentanone. The product is filtered off and dried, yielding 0.6 parts of cis-ethyl [4-{4-[2-(2,4-dichlorophenyl)-2-(1H-imidazol-1-ylmethyl-1,3-dioxolan-4-ylmethoxy]phenyl}-1-piperazinylcarbonyloxy-]acetate; mp. 146.6° C.

EXAMPLE IX

A mixture of 2.38 parts of 2-chloro-N-(4nitrophenyl-)acetamide, 4.8 parts of cis-1-{4-[2-(2,4-dichlorophenyl)-2-(1H-imidazol-1-ylmethyl)-1,3-dioxolan-4-ylmethoxy]phenyl}piperazine, 1.2 parts of N,N-diethylethanamine and 68 parts of N,N-dimethylformamide is stirred for 4.50 hours at 80° C. The reaction mixture is poured onto 400 parts of water and the product is extracted three times with dichloromethane. The combined extracts are washed three times with water, dried, filtered and evaporated. The residue is purified by column-chromatography over silica gel using a mixture of trichloromethane and methanol (98:2 by volume) as eluent. The pure fractions are collected and the eluent is evaporated. The residue solidifies on scratching in 2,2'-oxybispropane. The product is filtered off and dried, yielding 5.6 parts of cis-4-{4-[2-(2,4-dichlorophenyl)-2-(1H-imidazol-1-ylmethyl)-1,3-dioxolan-4-ylmethoxy]phenyl}-N-(4-nitrophenyl)-1-piperazineacetamide; mp. 151.1° C.

EXAMPLE X

Following the same procedure as described in Example IX and using equivalent amounts of the appropriate starting materials there are also prepared:
cis-4-{4-[2-(2,4-dichlorophenyl)-2-(1H-imidazol-1-ylmethyl)-1,3-dioxolan-4-ylmethoxy]phenyl}-N-(2,6-dimethylphenyl)-1-piperazineacetamide trihydrochloride monohydrate; mp. 209.3° C.;
cis-N-(2-chlorophenyl)-4-{4-[2-(2,4-dichlorophenyl)-2-(1H-imidazol-1-ylmethyl)-1,3-dioxolan-4-ylmethoxy]phenyl}-1-piperazineacetamide; mp. 124.7° C.;
cis-4-{4-[2-(2,4-dichlorophenyl)-2-(1H-imidazol-1-ylmethyl)-1,3-dioxolan-4-ylmethoxy]phenyl}-N-(2-methylphenyl)-1-piperazineacetamide; mp. 123.8° C.;
cis-4-{4-[2-(2,4-dichlorophenyl)-2-(1H-imidazol-1-ylmethyl)-1,3-dioxolan-4-ylmethoxy]-phenyl}-N-(4-methylphenyl)-1-piperazineacetamide; mp. 124.1° C.;
cis-4-{4-[2-(2,4-dichlorophenyl)-2-(1H-imidazol-1-ylmethyl)-1,3-dioxolan-4-ylmethoxy]-phenyl}-N-(2-methoxyphenyl)-1-piperazineacetamide; mp. 153.5° C.;
cis-4-{4-[2-(2,4-dichlorophenyl)-2-(1H-imidazol-1-ylmethyl)-1,3-dioxolan-4-ylmethoxy]-phenyl}-N-(4-methoxyphenyl)-1-piperazineacetamide; mp. 99.3° C.;
cis-N-(2,6-dichlorophenyl)-4-{4-[2-(2,4-dichlorophenyl)-2-(1H-imidazol-1-ylmethyl)-1,3-dioxolan-4-ylmethoxy]phenyl}-1-piperazineacetamide; mp. 127.2° C.;
cis-N-(4-chlorophenyl)-4-{4-[2-(2,4-dichlorophenyl)-2-(1H-imidazol-1-ylmethyl)-1,3-dioxolan-4-ylmethoxy]phenyl}-1-piperazineacetamide; mp. 138.1° C.;
cis-N-(2,4-dichlorophenyl)-4-{4-[2-(2,4-dichlorophenyl)-2-(1H-imidazol-1-ylmethyl)-1,3-dioxolan-4-ylmethoxy]phenyl}1-piperazineacetamide; mp. 105.5° C.;
cis-4-{4-[2-(2,4-dichlorophenyl)-2-(1H-imidazol-1-ylmethyl)-1,3-dioxolan-4-ylmethoxy]phenyl}-N,N-dimethyl-1-piperazineacetamide; mp. 158.5° C.;
cis-4-{4-[2-(2,4-dichlorophenyl)-2-(1H-imidazol-1-ylmethyl)-1,3-dioxolan-4-ylmethoxy]-phenyl}-N,N-diethyl-1-piperazineacetamide; mp. 120° C. and
cis-4-{4-[2-(2,4-dichlorophenyl)-2-(1H-imidazol-1-ylmethyl)-1,3-dioxolan-4-ylmethoxy]-phenyl}-N,N-dipropyl-1-piperazineacetamide ethanedioate (1:4); mp. 113.9° C.

EXAMPLE XI

A mixture of 16 parts of chloroacetonitrile, 100 parts of cis-1-{4-[2-(2,4-dichlorophenyl)-2-(1H-imidazol-1-ylmethyl)-1,3-dioxolan-4-ylmethoxy]phenyl} piperazine, 56.5 parts of N,N-diethylethanamine and 450 parts of N,N-dimethylformamide is stirred for 2 hours at 50° C. The reaction mixture is evaporated and the residue is stirred in water till the product is precipitated. It is filtered off and dissolved in dichloromethane. The organic phase is washed with water, dried, filtered and evaporated. The residue is purified by column-chromatography over silica gel using a mixture of trichloromethane and methanol (97:3 by volume) as eluent. The pure fractions are collected and the eluent is evaporated. The residue is crystallized from 4-methyl-2-pentanone, yielding 65 parts of cis-4-{4-[2-(2,4-dichlorophenyl)-2-(1H-imidazol-1-ylmethyl)-1,3-dioxolan-4-ylmethoxy]phenyl}-1-piperazineacetonitrile hemihydrate; mp. 124.8° C.

Following the same procedure and replacing chloroacetonitrile by 1-(2-chloroethyl)piperidine hydrochloride respectively N-(2-bromoethyl)benzenamine hydrobromide, there are also prepared:
cis-1-{4-[2-(2,4-dichlorophenyl)-2-(1H-imidazol-1-ylmethyl)-1,3-dioxolan-4-ylmethoxy]phenyl}-4-[2-(1-piperidinyl)ethyl]piperazine ethanedioate (1:3) dihydrate; mp. 133.6° C.;
cis-4-{4-[2-(2,4-dichlorophenyl)-2-(1H-imidazol-1-ylmethyl)-1,3-dioxolan-4-ylmethoxy]phenyl}-N-phenyl-1-piperazineethanamine ethanedioate (1:2); mp. 188.6° C.

EXAMPLE XII

A mixture of 32 parts of cis-2-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-1H-isoindole-1,3(2H)-dione, 4 parts of sodium hydroxide and 80 parts of 1-butanol is stirred and refluxed overnight. Another 4 parts of sodium hydroxide and 10 parts of water are added and stirring is continued for 6 hours at reflux. The reaction mixture is evaporated and a lot of water is added to the residue. Evaporation is continued and the product is extracted with dichloromethane. The extract is washed with water, dried, filtered and evaporated. The oily residue is converted into the hydrochloride salt in 2-propanone. The salt is filtered off and crystallized from a mixture of 2-propanol and ethanol, yielding 14.5 parts of cis-4-{4-[2-(2,4-dichlorophenyl)-2-(1H-imidazol-1-ylmethyl)-1,3-dioxolan-4-ylmethoxy]phenyl}-1-piperazineethanamine tetrahydrochloride.

A mixture of 10 parts of cis-4-{4-[2-(2,4-dichlorophenyl)-2-(1H-imidazol-1-ylmethyl)-1,3-dioxolan-4-ylmethoxy]phenyl}-1-piperazineacetonitrile and 200 parts of methanol saturated with ammonia is hydrogenated at normal pressure and at room temperature with 2 parts of rhodium-on-charcoal catalyst 5%. After the calculated amount of hydrogen is taken up, the catalyst is filtered off and the filtrate is evaporated. The oily residue is purified by column-chromatography over silica gel using a mixture of trichloromethane and methanol (90:10 by volume) saturated with ammonia, as eluent. The pure fractions are collected and the eluent is evaporated. The residue is crystallized from 1,1'-oxybispropane, yielding 2 parts of cis-4-{4-[2-(2,4-dichlorophenyl)-2-(1H-imidazol-1-ylmethyl)-1,3-dioxolan-4-ylmethoxy]phenyl}-1-piperazineethanamine monohydrate; mp. 104.2° C.

EXAMPLE XIII

To a stirred mixture of 2.7 parts of cis-4-{4-[2-(2,4-dichlorophenyl)-2-(1H-imidazol-1-ylmethyl)-1,3-dioxolan-4-ylmethoxy]phenyl}-1-piperazineethanamine, 5 parts of N,N-diethylethanamine and 65 parts of dichloromethane is added a solution of 0.8 parts of dimethylcarbamic chloride in a small amount of dichloromethane. Stirring at room temperature is continued for 6 hours. The reaction mixture is evaporated. The oily residue is dissolved in 2-propanone. The solution is filtered and the filtrate is evaporated. The oily residue is purified by column-chromatography over silica gel using a mixture of trichloromethane and methanol (95:5 by volume) as eluent. The pure fractions are collected and the eluent is evaporated. The oily residue is converted into the ethanedioate salt in 2-propanone. The salt is filtered off and crystallized twice from ethanol, yielding 2.3 parts of cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N',N'-dimethylurea ethanedioate (1:2) dihydrate; mp. 145.3° C.

In a similar manner there are also prepared:

cis-N-{2-[4-{4-[2-(2,4-dichlorophenyl)-2-(1H-imidazol-1-ylmethyl)-1,3-dioxolan-4-ylmetoxy]phenyl}-1-piperazinyl]ethyl}-N',N'-diethylurea ethanedioate (1:2) monohydrate; mp. 134.3° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-1-pyrrolidinecarboxamide ethanedioate (2:5) monohydrate; mp. 161.7° C.; and cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-4-morpholinecarboxamide ethanedioate (1:2) monohydrate; mp. 155.8° C.

EXAMPLE XIV

A mixture of 2.8 parts of isocyanatomethane, 5 parts of cis-4-{4-[2-(2,4-dichlorophenyl)-2-(1H-imidazol-1-ylmethyl)-1,3-dioxolan-4-ylmethoxy]phenyl}-1-piperazineethanol and 90 parts of methylbenzene is stirred and refluxed overnight. The reaction mixture is evaporated. The oily residue is purified by column-chromatography over silica gel using a mixture of trichloromethane and methanol (93.7 by volume) as eluent. The pure fractions are collected and the eluent is evaporated. The oily residue is crystallized from 2,2'-oxybispropane. The product is filtered off and dried, yielding 4 parts of cis-{2-[4-{4-[2-(2,4-dichlorophenyl)-2-(1H-imidazol-1-ylmethyl)-1,3-dioxolan-4-ylmethoxy]phenyl}-1-piperazinyl]ethyl}methylcarbamate; mp. 139.1° C.

Following the same procedure and using equivalent amounts of the appropriate starting materials there are also prepared:

cis-{2-[4-{4-[2-(2,4-dichlorophenyl)-2-(1H-imidazol-1-ylmethyl)-1,3-dioxolan-4-ylmethoxy]-phenyl}-1-piperazinyl]ethyl}ethylcarbamate ethanedioate (1:2) monohydrate; mp.170.7° C.;

cis-{2-[4-{4-[2-(2,4-dichlorophenyl)-2-(1H-imidazol-1-ylmethyl)-1,3-dioxolan-4-ylmethoxy]-phenyl}-1-piperazinyl]ethyl}propylcarbamate ethanedioate (2:5); mp. 187° C.;

cis-{2-[4-{4-[2-(2,4-dichlorophenyl)-2-(1H-imidazol-1-ylmethyl)-1,3-dioxolan-4-ylmethoxy]-phenyl}-1-piperazinyl]ethyl}phenylcarbamate ethanedioate (1:2); mp. 178.5° C. and cis-{2-[4-{4-[2-(2,4-dichlorophenyl)-2-(1H-imidazol-1-ylmethyl)-1,3-dioxolan-4-ylmethoxy]-phenyl}-1-piperazinyl]ethyl}(1-methylethyl)carbamate ethanedioate (1:2); mp. 161° C.

EXAMPLE XV

A mixture of 2.7 parts of cis-4-{4-[2-(2,4-dichlorophenyl)-2-(1H-imidazol-1-ylmethyl)-1,3-dioxolan-4-ylmethoxy]phenyl}-1-piperazineethanamine and 65 parts of dichloromethane is stirred till all solid enters solution. Then there is added a solution of 0.39 parts of isocyanatoethane in a small amount of dichloromethane. The whole is stirred for 1 hour at room temperature. The reaction mixture is evaporated and the residue is converted into the ethanedioate salt in ethanol. Upon scratching, the salt solidifies. It is filtered off and crystallized from ethanol, yielding 2.5 parts of cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-ethylurea ethanedioate (1:2) hemihydrate; mp. 126.4° C.

EXAMPLE XVI

Following the same procedure as described in Example XV and using equivalent amounts of the appropriately substituted amines and the appropriate isocyanates or isothiocyanates there are also prepared:

cis-N-{2-[4-{4-[2(2,4-dichlorophenyl)-2-(1H-imidazol-1-ylmethyl)-1,3-dioxolan-4-ylmethoxy]phenyl}-1-piperazinyl]ethyl}-N'-methylurea monohydrate; mp. 102.7° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-propylurea ethanedioate (1:2) monohydrate; mp. 125.3° C.;

cis-N-butyl-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl urea ethanedioate (1:2) monohydrate; mp. 103.3° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-phenylurea ethanedioate (1:2); mp. 183.9° C.;

cis-N-{2-[4-}4-[2-(2,4-dichlorophenyl)-2-1H-imidazol-1-ylmethy)-1,3-dioxolan-4-ylmethoxy]phenyl}-1-piperazinyl]-ethyl}-N'-(4-methylphenyl urea ethanedioate (1:2) monohydrate; mp. 167° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-(4-methylphenyl)urea ethanedioate (1:2) monohydrate; mp. 167° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-(2,6-dimethylphenyl)urea ethanedioate (1:2) monohydrate; mp. 142° C.;

cis-N-{2-[4-{4-[2-(2,4-dichlorophenyl)-2-(1H-imidazol-1-ylmethyl)-1,3-dioxolan-4-ylmethoxy]phenyl}-1- piperazinyl]ethyl}-N'-(4-methoxyphenyl)urea ethanedioate (1:2); mp. 172.8° C.;

cis-N-(4-chlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}urea ethanedioate (1:1) monohydrate; mp. 189.6° C.;

cis-N-(2,6-dichlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}urea ethanedioate (1:2); mp. 170.1° C.;

cis-N-(2,4-dichlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}urea ethanedioate (1:1) dihydrate; mp. 157.2° C.;

cis-N-{2-[4-{4-[2-(2,4-dichlorophenyl)-2-(1H-imidazol-1-ylmethyl-1,3-dioxolan-4-ylmethoxy]phenyl}-1-piperazinyl]ethyl}-N'-methylthiourea; mp. 163.7° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-ethylthiourea ethanedioate (1:2); mp. 172.3° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-(2-methoxypropyl)thiourea ethanedioate (1:2); mp. 146.6° C.;

cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-phenylthiourea ethanedioate (1:2); mp. 185.2° C.;

cis-N-(2-chlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}thiourea ethanedioate (1:2); mp. 176° C.;

cis-N-(4-chlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}thiourea ethanedioate (1:2); mp. 214.7° C.;

cis-N-(2,4-dichlorophenyl)-N'-{2-[4-{4-[2-(2,4-dichlorophenyl)-2-(1H-imidazol-1-ylmethyl)-1,3-dioxolan-4-ylmethoxy]phenyl}-1-piperazinyl]ethyl}thiourea ethanedioate (1:2); mp. 171° C.; and cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}-N'-(4-methoxyphenyl)thiourea ethanedioate (1:2); mp. 197.8° C.

EXAMPLE XVII

A mixture of 60 parts of formic acid, 5 parts of cis-4-{4-[2-(2,4-dichlorophenyl)-2-(1H-imidazol-1-ylmethyl)-1,3-dioxolan-4-ylmethoxy]phenyl}-1-piperazineethanol and 5 parts of acetic acid anhydride is stirred and refluxed for 2 hours. The reaction mixture is evaporated and the residue is taken up in water. Sodium hydrogen carbonate is added and the whole is stirred for 10 minutes at room temperature. The product is extracted with dichloromethane. The extract is dried, filtered and evaporated. The oily residue is crystallized from a mixture of benzene and petroleumether. The product is filtered off and recrystallized from 4-methyl-2-pentanone, yielding 2.5 parts of cis-{2-[4-{4-[2-(2,4-dichlorophenyl)-2-(1H-imidazol-1-ylmethyl)-1,3-dioxolan-4-ylmethoxy]phenyl}-1-piperazinyl]ethyl}formate; mp. 109.1° C.

EXAMPLE XVIII

A mixture of 12 parts of formic acid and 2.7 parts of cis-4-{4-[2-(2,4-dichlorophenyl)-2-(1H-imidazol-1-ylmethyl)-1,3-dioxolan-4-ylmethoxy]phenyl}-1-piperazineethanamine is stirred and refluxed overnight. The reaction mixture is evaporated. The oily residue is dissolved in water and the solution is neutralized with sodium hydrogen carbonate. The product is extracted with trichloromethane. The extract is dried, filtered and evaporated. The residue is purified by column-chromatography over silica gel using a mixture of trichloromethane and methanol (98:2 by volume) saturated with ammonium hydroxide, as eluent. The pure fractions are collected and the eluent is evaporated. The residue is crystallized from 4-methyl-2-pentanone, yielding 0.7 parts of cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}formamide; mp. 152.4° C.

EXAMPLE XIX

A mixture of 10 parts of acetic acid anhydride, 5 parts of cis-4-{4-[2-(2,4-dichlorophenyl)-2-(1H-imidazol-1-ylmethyl)-1,3-dioxolan-4-ylmethoxy]phenyl}-1-piperazine ethanol and 130 parts of dichloromethane is stirred and refluxed for 1 hour. The reaction mixture is evaporated. The oily residue solidifies on scratching in 2,2'-oxybispropane. The product is filtered off and crystallized from a mixture of benzene and petroleumether, yielding 3.6 parts of cis-{2-[4-{4-[2-(2,4-dichlorophenyl)-2-(1H-imidazol-1-ylmethyl)-1,3-dioxolan-4-ylmethoxy]phenyl}-1-piperazinyl]ethyl}acetate; mp. 174.7° C.

In a similar manner there are also prepared:

cis-{2-[4-{4-[2-(2,4-dichlorophenyl)-2-(1H-imidazol-1-ylmethyl)-1,3-dioxolan-4-ylmethoxy]phenyl}-1-piperazinyl]ethyl}propanoate; mp. 145.9° C.; and cis-{2-[4-{4-[2-(2,4-dichlorophenyl)-2-(1H-imidazol-1-ylmethyl)-1,3-dioxolan-4-ylmethoxy]phenyl}-1-piperazinyl]ethyl}butanoate; mp. 96.6° C.

EXAMPLE XX

To a stirred mixture of 2.7 parts of cis-N-4 {4-[2-(2,4-dichlorophenyl)-2-(1H-imidazol-1-ylmethyl)-1,3-dioxolan-4-ylmethoxy]phenyl}-1-piperazineethanamine and 130 parts of dichloromethane is added 1 part of acetic acid anhydride and stirring is continued overnight at room temperature. The reaction mixture is washed with a sodium hydrogen carbonate solution, dried, filtered and evaporated. The oily residue is converted into the ethanedioate salt in 2-propanone. The salt is filtered off and crystallized from a mixture of acetonitrile and ethanol, yielding 3 parts of cis-N-{2-[4-{4-[2-(2,4-dichlorophenyl)-2-(1H-imidazol-1-ylmethyl)-1,3-dioxolan-4-ylmethoxy]phenyl}-1-piperazinyl]ethyl}acetamide ethanedioate (1:2) monohydrate; mp. 139.1° C.

EXAMPLE XXI

A mixture of 3.5 parts of cis-4-{4-[2-(2,4-dichlorophenyl)-2-(1H-imidazol-1-ylmethyl)-1,3-dioxolan-4-ylmethoxy]phenyl}-1-piperazineethanamine and 65 parts of dichloromethane is stirred till all solid enters solution. Then there are added 1 part of sodium hydrogen carbonate and 50 parts of water. While stirring vigorously, 0.7 parts of methyl carbonochloridate are added and the whole is stirred for 3 hours at room temperature. The organic phase is separated, washed with water, dried, filtered and evaporated. The oily residue is purified by column-chromatography over silica gel using a mixture of trichloromethane and methanol (95:5 by volume) as eluent. The pure fractions are collected and the eluent is evaporated. The residue is converted into the ethanedioate salt in methanol. The salt is filtered off and dried, yielding 3.5 parts of cis-methyl{2-[4-{4-[2-(2,4-dichlorophenyl)-2-(1H-imidazol-1-ylmethyl)-1,3-dioxolan-4-ylmethoxy]phenyl}-1-piperazinyl]ethyl}carbamate ethanedioate (1:2) dihydrate; mp. 168.9° C.

In a similar manner there are also prepared:

cis-ethyl{2-[4-{4-[2-(2,4-dichlorophenyl)-2-(1H-imidazol-1-ylmethyl)-1,3-dioxolan-4-ylmethoxy]phenyl}-1-piperazinyl]ethyl}carbamate ethanedioate (1:2) monohydrate; mp. 164.1° C.; and cis-phenyl{2-[4-{4-[2-(2,4-dichlorophenyl)-2-(1H-imidazol-1-ylmethyl)-1,3-dioxolan-4-ylmethoxy]phenyl}-1-piperazinyl]ethyl}carbamate ethanedioate (1:2); mp. 179.6° C.

EXAMPLE XXII

A mixture of 5 parts of cis-4-{4-[2-(2,4-dichlorophenyl)-2-(1H-imidazol-1-ylmethyl)-1,3-dioxolan-4-ylmethoxy]-phenyl}-1-piperazineethanol, 6 parts of N,N-diethylethanamine and 130 parts of dichloromethane is stirred till 1 solid enters solution. Then there are added 2.7 parts of 2-methylpropanoyl chloride and the whole is stirred and refluxed for 2 hours. The reaction mixture is cooled and washed with water. The organic phase is dried, filtered and evaporated. The oily residue is purified by column-chromatography over silica gel using a mixture of trichloromethane and methanol (95:5 by volume) as eluent. The pure fractions are collected and the eluent is evaporated. The residue is converted into the ethanedioate salt in ethanol and 1,1'-oxybisethane. The salt is filtered off and crystallized from ethanol, yielding 3.5 parts of cis-{2-[4-{4-[2-(2,4-dichlorophenyl)-2-(1H-imidazol-1-ylmethyl)-1,3-dioxolan-4-ylmethoxy]-phenyl}-1-piperazinyl]ethyl}2-methylpropanoate ethanedioate (1:2) monohydrate; mp. 156.5° C.

EXAMPLE XXIII

A mixture of 2 parts of 1-chloro-3-(chloromethyl)benzene, 4.9 parts of cis-1-{4-[2-(2,4-dichlorophenyl)-2-(1H-imidazol-1-ylmethyl)-1,3-dioxolan-4-ylmethoxy]phenyl}piperazine, 1.2 parts of N,N-diethylethanamine and 68 parts of N,N-dimethylformamide is stirred and heated for 3.50 hours at 80° C. The whole is further stirred over week-end at room temperature. The reaction mixture is poured onto water and the product is extracted three times with benzene. The combined extracts are washed three times with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in 2,2'-oxybispropane, yielding 3.4 parts of cis-1-(3-chlorophenylmethyl)-4-{4-[2-(2,4-dichlorophenyl)-2-(1H-imidazol-1-ylmethyl)-1,3-dioxolan-4-ylmethoxy]phenyl}piperazine; mp. 109.9° C.

EXAMPLE XXIV

There are also prepared following the same procedure as described in Example XXIII and using equivalent amounts of the appropriate starting materials:

cis-1-(2-chlorophenylmethyl)-4-{4[2-(2,4-dichlorophenyl)-2-(1H-imidazol-1-ylmethyl)-1,3-dioxolan-4-ylmethoxy]phenyl}piperazine; mp. 108.8° C.;

cis-1-(4-chlorophenylmethyl)-4-{4-[2-(2,4-dichlorophenyl)-2-(1H-imidazol-1-ylmethyl)-1,3-dioxolan-4-ylmethoxy]phenyl}piperazine; mp. 126.3° C.;

cis-1-{4-[2-(2,4-dichlorophenyl)-2-(1H-imidazol-1-ylmethyl)-1,3-dioxolan-4-ylmethoxy]-phenyl}-4-(2,4-dichlorophenylmethyl)piperazine; mp. 112.4° C.;

cis-1-{4-[2-(2,4-dichlorophenyl)-2-(1H-imidazol-1-ylmethyl)-1,3-dioxolan-4-ylmethoxy]-phenyl}-4-(2,6-dichlorophenylmethyl)piperazine; mp. 134° C.;

cis-1-{4-[2-(2,4-dichlorophenyl)-2-(1H-imidazol-1-ylmethyl)-1,3-dioxolan-4-ylmethoxy]-phenyl}-4-(2,5-dimethylphenylmethyl)piperazine; mp. 100.3° C.

cis-1-{4-[2-(2,4-dichlorophenyl)-2-(1H-imidazol-1-ylmethyl)-1,3-dioxolan-4-ylmethoxy]-phenyl}-4-[3-(trifluoromethyl)phenylmethyl]piperazine ethanedioate (2:5); mp. 207.2° C.;

cis-1-(2-chloro-4-nitrophenylmethyl)-4-{4-[2-(2,4-dichlorophenyl)-2-(1H-imidazol-1-ylmethyl)-1,3-dioxolan-4-ylmethoxy]phenyl}piperazine; mp. 124.5° C.

cis-1-{4-[2-(2,4-dichlorophenyl)-2-(1H-imidazol-1-ylmethyl)-1,3-dioxolan-4-ylmethoxy]phenyl}-4-(4-nitrophenylmethyl)piperazine; mp. 160.5° C.;

cis-1-[2-(4-chlorophenyl)ethyl]-4-{4-[2,4-dichlorophenyl)-2-(1H-imidazol-1-ylmethyl)-1,3-dioxolan-4-ylmethoxy]phenyl}piperazine; mp. 106°–108° C.;

cis-1-(4-bromophenylmethyl)-4-{4-[2-(2,4-dichlorophenyl)-2-(1H-imidazol-1-ylmethyl)-1,3-dioxolan-4-ylmethoxy]phenyl}piperazine hemihydrate; mp. 118.8° C.;

cis-1-{4-[2-(2,4-dichlorophenyl)-2-(1H-imidazol-1-ylmethyl)-1,3-dioxolan-4-ylmethoxy]phenyl}-4-(4-fluorophenylmethyl)piperazine; mp. 137.9° C.;

cis-1-{4-[2-(2,4-dichlorophenyl)-2-(1H-imidazol-1-ylmethyl)-1,3-dioxolan-4-ylmethoxy]phenyl}-4-(4-methylphenylmethyl)piperazine; mp. 109.8° C.;

cis-1-{4-[2-(2,4-dichlorophenyl)-2-(1H-imidazol-1-ylmethyl)-1,3-dioxolan-4-ylmethoxy]-phenyl}-4-(4-methoxyphenylmethyl)piperazine; mp. 113.3° C.;

cis-1-{4-[2-(2,4-dichlorophenyl)-2-(1H-imidazol-1-ylmethyl)-1,3-dioxolan-4-ylmethoxy]phenyl}-4-[2-(4-methoxyphenyl)ethyl]piperazine; mp. 137.9° C.;

cis-1-(4-chlorophenylmethyl)-4-{4-[2-(2,4-dichlorophenyl)-2-(1H-1,2,4-triazol-1-ylmethyl)-1,3-dioxolan-4-ylmethoxy]phenyl}piperazine; mp. 125.1° C.;

cis-1-(2-chlorophenylmethyl)-4-{4-[2-(2,4-dichlorophenyl)-2-(1H-1,2,4-triazol-1-ylmethyl)-1,3-dioxolan-4-ylmethoxy]phenyl}piperazine; mp. 92.5° C.;

cis-1-[2-(4-chlorophenyl)ethyl]-4-{4-[2-(2,4-dichlorophenyl)-2-(1H-1,2,4-triazol-1-ylmethyl)-1,3-dioxolan-4-ylmethoxy]phenyl}piperazine; mp. 120° C.;

cis-1-(4-bromophenylmethyl)-4-{4-[2-(2,4-dichlorophenyl)-2-(1H-1,2,4-triazol-1-ylmethyl)-1,3-dioxolan-4-ylmethoxy]phenyl}piperazine; mp. 139.2° C.;

cis-1-{4-[2-(2,4-dichlorophenyl)-2-(1H-1,2,4-triazol-1-ylmethyl)-1,3-dioxolan-4-ylmethoxy]phenyl}-4-(4-fluorophenylmethyl)piperazine; mp. 111.5° C.;

cis-1-(2,4-dichlorophenylmethyl)-4-{4-[2-(2,4-dichlorophenyl)-2-(1H-1,2,4-triazol-1-ylmethyl)-1,3-dioxolan-4-ylmethoxy]phenyl}piperazine; mp. 118.8° C.;

cis-1-{4-[2-(2,4-dichlorophenyl)-2-(1H-1,2,4-triazol-1-ylmethyl)-1,3-dioxolan-4-ylmethoxy]phenyl}-4-(4-methylphenylmethyl)piperazine; mp. 123.4° C.;

cis-1-{4-[2-(2,4-dichlorophenyl)-2-(1H-1,2,4-triazol-1-ylmethyl)-1,3-dioxolan-4-ylmethoxy]phenyl}-4-(2,5-dimethylphenylmethyl)piperazine; mp. 100.2° C.;

cis-1-{4-[2-(2,4-dichlorophenyl)-2-(1H-1,2,4-triazol-1-ylmethyl)-1,3-dioxolan-4-ylmethoxy]phenyl}-4-(4-methoxyphenylmethyl)piperazine; mp. 112° C.;

cis-1-{4-[2-(2,4-dichlorophenyl)-2-(1H-1,2,4-triazol-1-ylmethyl)-1,3-dioxolan-4-ylmethoxy]phenyl}-4-[2-(4-methoxyphenyl)ethyl]piperazine; mp. 139.9° C.;

cis-1-{4-[2-(2,4-dichlorophenyl)-2-(1H-imidazol-1-ylmethyl)-1,3-dioxolan-4-ylmethoxy]phenyl}-4-(2-pyridinylmethyl)piperazine; mp. 111.3° C.;

cis-1-{4-[2-(2,4-dichlorophenyl)-2-(1H-imidazol-1-ylmethyl)-1,3-dioxolan-4-ylmethoxy]phenyl}-4-(3-pyridinylmethyl)piperazine; mp. 100.9° C.;

cis-1-{4-[2-(2,4-dichlorophenyl)-2-(1H-imidazol-1-ylmethyl)-1,3-dioxolan-4-ylmethoxy]phenyl}-4-(4-pyridinylmethyl)piperazine; mp. 110.6° C.;

cis-1-{4-[2-(2,4-dichlorophenyl)-2-(1H-1,2,4-triazol-1-ylmethyl)-1,3-dioxolan-4-ylmethoxy]phenyl}-4-(4-pyridinylmethyl)piperazine; mp. 98.2° C.;

cis-1-{4-[2-(2,4-dichlorophenyl)-2-(1H-1,2,4-triazol-1-ylmethyl)-1,3-dioxolan-4-ylmethoxy]phenyl}-4-(2-pyridinylmethyl)piperazine; mp. 104.4° C.; and cis-1-{4-[2-(2,4-dichlorophenyl)-2-(1H-1,2,4-triazol-1-ylmethyl)-1,3-dioxolan-4-ylmethoxy]phenyl}-4-(3-pyridinylmethyl)piperazine; mp. 106.2° C.

EXAMPLE XXV

To 1 part of a solution of 2 parts of thiophene in 40 parts of ethanol are added 4 parts of 2-propanone, 2.7 parts of cis-4-{4-[2-(2,4-dichlorophenyl)-2-(1H-imidazol-1-ylmethyl)-1,3-dioxolan-4-ylmethoxy]phenyl}-1-piperazineethanamine and 120 parts of methanol. The whole is hydrogenated at normal pressure and at room temperature with 2 parts of platinum-on-charcoal catalyst 5%. After the calculated amount of hydrogen is taken up, the catalyst is filtered off and the filtrate is evaporated. The residue is converted into the ethanedioate salt in 2-propanone. The salt is filtered off and crystallized from a mixture of ethanol and 2-propanone, yielding 2.7 parts of cis-4-{4-[2-(2,4-dichlorophenyl)-2-(1H-imidazol-1-ylmethyl)-1,3-dioxolan-4-ylmethoxy]phenyl}-N-(1-methylethyl)-1-piperazineethanamine ethanedioate (1:3). dihydrate; mp. 128.3° C.

EXAMPLE XXVI 4.6 Parts of cis+trans-1-[3-(4-chlorophenyl)-1-oxo-2-propenyl]-4-{4-[2-(2,4-dichlorophenyl)-2-(1H-1,2,4-triazol-1-ylmethyl)-1,3-dioxolan-4-ylmethoxy]phenyl}piperzine are purified by column-chromatography over silica gel using a mixture of trichloromethane, hexane and methanol (48:48:4 by volume) as eluent. The fractions, containing the cis-isomer, are collected and the eluent is evaporated. The residue is crystallized from 4-methyl-2-pentanone. The product is filtered off and dried, yielding 1.9 parts of cis-1-[3-(4-chlorophenyl)-1-oxo-2-propenyl]-4-[4-[2-(2,4-dichlorophenyl)-2-(1H-1,2,4-triazol-1-ylmethyl)-1,3-dioxolan-4-ylmethoxy]phenyl}piperazine; mp. 185° C.

EXAMPLE XXVII

A mixture of 6.8 parts of cis-N-{4-[4-4-[2-(2,4-dichlorophenyl)-2-(1H-imidazol-1-ylmethyl)-1,3-dioxolan-4-ylmethoxy]phenyl}-1-piperazinylsulfonyl]phenyl acetamide, 0.8 parts of sodium hydroxide and 80 parts of 1-butanol is stirred and refluxed overnight. Benzene is added and the whole is washed with water. The solvent is evaporated. The residue is triturated in a mixture of 4-methyl-2-pentanone and 2,2'-oxybispropane. The product is filtered off and crystallized from 4-methyl-2-pentanone, yielding 6.2 parts (94%) of cis-1-(4-aminophenylsulfonyl)-4-{4-[2-(2,4-dichlorophenyl)-2-(1H-imidazol-1-ylmethyl)-1,3-dioxolan-4-ylmethoxy]phenyl}-piperazine monohydrate; mp. 147.8° C.

What is claimed is:

1. A chemical compound selected from the group consisting of a compound having the formula:

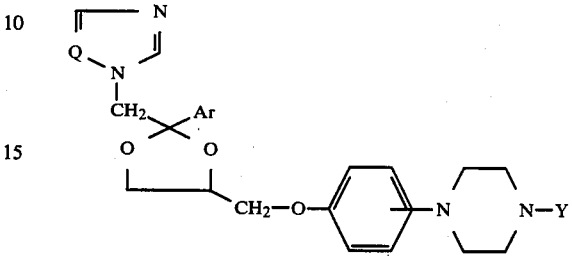

and the pharmaceutically acceptable acid addition salts and stereochemically isomeric forms thereof, wherein:

Q is a member selected from the group consisting of N and CH;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is a member selected from the group consisting of:

a radical of the formula

(a)

wherein $R^1$ is selected from the group consisting of trifluoromethyl and aryl;

a radical of formula

(b)

wherein alk is a member selected from the group consisting of lower alkylene and lower alkenylene and $R^2$ is a member selected from the group consisting of cyano, amino, mono- and di(aryllower alkyl)amino, 1-pyrrolidinyl, 1-morpholinyl, 1-piperidinyl, aryloxy and aryl, provided that alk is other than methylene when $R^2$ is phenyl;

a radical of formula

(c)

wherein n is an integer of from 0 to 6 inclusive, X is O or S and $R^3$ is selected from the group consisting of hydrogen, mono-, di- and trihalolower alkyl, amino, mono- and di(lower alkyl)amino, arylamino, mono- and di(aryllower alkyl)amino, aminolower alkyl, mono- and di(lower alkyl)aminolower alkyl, (1-pyrrolidinyl)lower alkyl, (1-morpholinyl)lower alkyl, (1-piperidinyl)lower alkyl, aryl, aryllower alkyl, aryllower alkenyl and lower alkyloxycarbonyllower alkyloxy, provided that:

(i) said n is other than 0 or 1 when said $R^3$ is amino or lower alkylamino; and (ii) said n is other than 0 when said $R^3$ is di(lower alkyl)amino or aryl or hydrogen; and a radical of formula

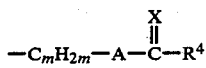
(d)

wherein m is an integer of from 1 to 6 inclusive, A is O or NH, X is O or S and $R^4$ is a member selected from the group consisting of hydrogen, lower alkyl, lower alkyloxy, aryl, aryloxy, aryllower alkyl, amino, mono- and di(lower alkyl)amino, arylamino, mono- and di(aryllower alkyl)amino, 1-pyrrolidinyl, 1-morpholinyl and 1-piperidinyl;

wherein said aryl, as used in the foregoing definitions, is selected from the group consisting of phenyl, substituted phenyl, thienyl, halothienyl, lower alkylthienyl and pyridinyl, said substituted phenyl having from 1 to 3 substituents each independently selected from the group consisting of lower alkyl, lower alkyloxy, halo, amino, mono- and di(lower alkyl)amino, lower alkylcarbonylamino, nitro and trifluoromethyl.

2. A chemical compound selected from the group consisting of cis-ethyl[4-{4-[2-(2,4-dichlorophenyl)-2-(1H-imidazol-1-ylmethyl)-1,3-dioxolan-4-ylmethoxy]-phenyl}-1-piperazinylcarbonyloxy]acetate and the pharmaceutically acceptable acid addition salts and stereochemically isomeric forms thereof.

3. A chemical compound selected from the group consisting of cis-4-{4-[2-(2,4-dichlorophenyl)-2-(1H-imidazol-1-ylmethyl)-1,3-dioxolan-4-ylmethoxy]-phenyl}-N-(2-methylphenyl)-1-piperazineacetamide and the pharmaceutically acceptable acid addition salts and stereochemically isomeric forms thereof.

4. A chemical compound selected from the group consisting of cis-N-(2,6-dichlorophenyl)-4-{4-[2-(2,4-dichlorophenyl)-2-(1H-imidazol-1-ylmethyl)-1,3-dioxolan-4-ylmethoxy]phenyl}-1-piperazineacetamide and the pharmaceutically acceptable acid addition salts and stereochemically isomeric forms thereof.

5. A composition for combatting a microorganism selected from the group consisting of fungus and bacterium comprising an inert carrier material and as an active ingredient an effective antifungal or antibacterial amount of a compound selected from the group consisting of a compound having the formula:

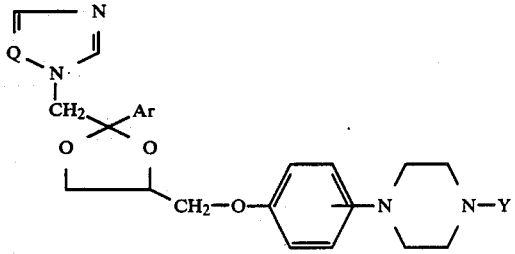

and the pharmaceutically acceptable acid addition salts and stereochemically isomeric forms thereof, wherein:

Q is a member selected from the group consisting of N and CH;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is a member selected from the group consisting of:

a radical of the formula $$-SO_2-R^1 \qquad (a)$$

wherein $R^1$ is selected from the group consisting of trifluoromethyl and aryl;

a radical of formula $$-alk-R^2 \qquad (b)$$

wherein alk is a member selected from the group consisting of lower alkylene and lower alkenylene and $R^2$ is a member selected from the group consisting of cyano, amino, mono- and di(lower alkyl)amino, arylamino, mono- and di(aryllower alkyl)amino, 1-pyrrolidinyl, 1-morpholinyl, 1-piperidinyl, aryloxy and aryl, provided that alk is other than methylene when $R^2$ is phenyl;

a radical of formula

(c)

wherein n is an integer of from 0 to 6 inclusive, X is O or S and $R^3$ is selected from the group consisting of hydrogen, mono-, di- and trihalolower alkyl, amino, mono- and di(lower alkyl)amino, arylamino, mono- and di(aryllower alkyl)amino, aminolower alkyl, mono- and di(lower alkyl)aminolower alkyl, (1-pyrrolidinyl)lower alkyl, (1-morpholinyl)lower alkyl, (1-piperidinyl)lower alkyl, aryl, aryllower alkyl, aryllower alkenyl and lower alkyloxycarbonyllower alkyloxy, provided that (i) said n is other than 0 or 1 when said $R^3$ is amino or lower alkylamino; and (ii) said n is other than 0 when said $R^3$ is di(lower alkyl)amino or aryl or hydrogen; and a radical of formula

(d)

wherein m is an integer of from 1 to 6 inclusive, A is O or NH, X is O or S and $R^4$ is a member selected from the group consisting of hydrogen, lower alkyl, lower alkyloxy, aryl, aryloxy, aryllower alkyl, amino, mono- and di(lower alkyl)amino, arylamino, mono- and di(aryllower alkyl)amino, 1-pyrrolidinyl, 1-morpholinyl and 1-piperidinyl;

wherein said aryl, as used in the foregoing definitions, is selected from the group consisting of phenyl, substituted phenyl, thienyl, halothienyl, lower alkylthienyl and pyridinyl, said substituted phenyl having from 1 to 3 substituents each independently selected from the group consisting of lower alkyl, lower alkyloxy, halo, amino, mono- and di(lower alkyl)amino, lower alkylcarbonylamino, nitro and trifluoromethyl.

6. A chemical compound selected from the group consisting of cis-1-{4-[2-(2,4-dichlorophenyl)-2-(1H-imidazol-1-ylmethyl)-1,3-dioxolan-4-ylmethoxy]-phenyl}-4-(2-pyridinylmethyl)piperazine and the pharmaceutically acceptable acid addition salts and stereochemically isomeric forms thereof.

* * * * *

UNITED STATES PATENT AND TRADEMARK OFFICE
CERTIFICATE OF CORRECTION

PATENT NO. : 4,503,055

DATED : March 5, 1985

INVENTOR(S) : Heeres et al.

It is certified that error appears in the above—identified patent and that said Letters Patent is hereby corrected as shown below:

Claim 1, col. 26, line 45 after "amino" insert --mono-and di(loweralkyl) amino, arylamino --

Signed and Sealed this

First Day of July 1986

[SEAL]

Attest:

DONALD J. QUIGG

Attesting Officer

Commissioner of Patents and Trademarks